United States Patent [19]

Ostoich

[11] 4,211,741
[45] Jul. 8, 1980

[54] EXTRUSION PROCESS FOR LAMINATED MEDICAL-SURGICAL TUBING

[75] Inventor: Eli Ostoich, Greenfield, Wis.

[73] Assignee: Sunlite Plastics, Inc., Milwaukee, Wis.

[21] Appl. No.: 875,929

[22] Filed: Feb. 8, 1978

Related U.S. Application Data

[62] Division of Ser. No. 785,440, Apr. 7, 1977, abandoned.

[51] Int. Cl.² .............................................. B29F 3/10
[52] U.S. Cl. .................................... 264/173; 128/348; 264/236
[58] Field of Search ................. 264/173, 236, 174; 128/348

[56] References Cited

U.S. PATENT DOCUMENTS

| | | | |
|---|---|---|---|
| 3,277,225 | 10/1966 | Heard | 264/174 |
| 3,404,432 | 10/1968 | White et al. | 264/174 |
| 3,411,981 | 11/1968 | Thomas | 264/174 |
| 3,538,207 | 11/1970 | Toole | 264/174 |
| 3,538,209 | 11/1970 | Hegler | 264/173 |
| 3,561,493 | 4/1965 | Maillard et al. | 264/173 |
| 3,880,691 | 4/1975 | Pannenbecker et al. | 264/173 |

*Primary Examiner*—Jay H. Woo
*Attorney, Agent, or Firm*—Andrus, Sceales, Starke & Sawall

[57] ABSTRACT

A coextruded multiple layered medical-surgical tubing employs a first layer of polyvinyl chloride and a second layer of polyurethane laminated as an integral multilayer tube. The polyurethane creates a non-migrating medical-surgical tubing. The polyvinyl chloride and polyurethane are coextruded with the polyurethane heated at a curing temperature of 400° to 450° F. and the polyvinyl heated to a temperature of 300° F. and rapidly cooled. The coextruded tubing then may pass through a cooling unit which rapidly reduces the temperature of the coextruded polyvinyl-polyurethane tubing medical-surgical tubing and positively prevents destruction of the polyvinyl layer as a result of the high temperature of the polyurethane. The relative quantity of thickness of the inexpensive plastic and the polyurethane layers are selected to provide any desired characteristic; such as hardness and flexibility, coupler adaptability and the like.

5 Claims, 4 Drawing Figures

EXTRUSION PROCESS FOR LAMINATED MEDICAL-SURGICAL TUBING

This is a division of application, Ser. No. 785,440, filed Apr. 7, 1977, now abandoned.

BACKGROUND OF THE INVENTION

The present invention relates to multiple layered laminated medical-surgical tubing employing different layers of different plastic materials.

Medical-surgical tubings are widely employed in the medical field for analysis and treatment of patients. Generally, such tubing is made of an extruded plastic material. For example, polyethylene is widely employed in surgical tubing. U.S. Pat. No. 3,618,614, for example, discloses a multiple wall surgical tubing for stomach, thoracic or rectal use wherein like plastics such as polyethylene are bonded together. One of the layers is provided with a radiopaque material and the other is a clear tube. The composite tube may therefore be readily observed by fluoroscopic apparatus. The clear layer provides the desired physical characteristic such as smoothness or hardness. Vinyl plastic layers may also be similarly formed to provide radiopaque medical-surgical tubing.

In various applications, particularly for transporting of blood, interveneous fluids and the like, the migrating characteristic of the plastic employed must be carefully considered to prevent unacceptable contamination of the fluid. Thus, in dialysis equipment for treatment of kidney disease and the like, it is extremely important that there be essentially no contamination of the blood. In such medical application, polyvinyl chloride (PVC) is widely employed as the material for the medical-surgical tubing. Such material is basically, however, a clear brittle thermoplastic. In order to convert such brittle material into a flexible material, suitable plasticizors are added and may form as much as 50% of the finished product. In addition, lubricants and stabilizers may also be required. Although such materials are presently employed for medical applications, the possible migrating characteristic of additive materials demands careful attention in the manufacture and use. A polyurethane tubing has been suggested for such use because it is a stable material which is a relatively soft, flexible material without essentially any additives, and therefore minimizes possibility of migration of contaminants into or from the fluid. Polyurethane also has good flow characteristics and thus has many significant advantages. The cost, however, is significantly greater than polyvinyl chloride and such use has generally been limited to exceptional biological blood compatability applications. The terminology medical-surgical tubing is employed to define that unique class of tubing employed in the in vivo treatment of human patients and wherein the tubing is introduced into the patient's body or otherwise connected thereto for transfer of fluids and is otherwise used in the analysis and study of fluids related to treatment of human patients.

Although various medical-surgical tubing is therefore readily available for the various analysis, there is a very significant need for a low cost nonmigratory medical-surgical tubing where exceptional high degrees of purity are demanded.

SUMMARY OF THE PRESENT INVENTION

The present invention is particularly directed to a coextruded multiple layered medical tubing employing a first layer of relavtively inexpensive plastic material such as polyvinyl chloride and a second layer of polyurethane laminated as an integral multi-layer tubing. Polyurethane curing requires a significantly higher temperature than polyvinyl chloride or other conventional low cost plastics and such characteristics would indicate that the materials cannot be directly laminated without destroying or at least significantly adversely effecting the conventional plastic layer. The present inventor, however, has found that by proper co-extrusion of the materials and in particular, the separate heating to the respective curing temperatures, a laminated tubing with a firm continuous interface and without destruction of the low temperature curing plastics is obtained. The polyurethane layer can be made of any desired thickness including a very minimal thickness sufficient to maintain a continuous coating or covering thereby creating an essentially truly non migrating medical-surgical tubing in a rapid and efficient manner, and at reasonable cost. Thus, each of the materials is extruded at the proper temperature for curing and bonding, but the period of a high temperature is sufficient to the effective desired bond, but insufficient to cause any adverse destruction or degradation of the low temperature plastic. In a preferred embodiment, the multiple layered coextruded tubing is rapidly cooled shortly downstream of the extrusion nozzle unit to further minimize the effective heating of the low temperature curing plastic by the high temperature of the polyurethane.

In a particular and highly effective construction polyvinyl chloride and polyurethane are coextruded with the polyurethane heated at a curing temperature of 400° to 450° F. and a polyvinyl heated to a temperature of 300° F. The coextruded tubing passes through a cooling unit which rapidly reduces the temperature of the coextruded polyvinyl-polyurethane tubing medical-surgical tubing.

The relative quantity or thickness of the inexpensive plastic and the polyurethane layers may be selected to provide any desired characteristic. Thus, generally, polyurethane is a relatively flexible plastic material having a hardness of 80 to 90 durometers. In contrast, polyvinyl chloride plastic is readily available with a durometer rating of 40 to 95. For a minimal cost tubing, the polyurethane layer will be selected with a very minimum thickness. Although any thickness can be employed, varying up to 99% of the total thickness, generally the thickness should be extruded to be on the order of a minimum of 1 mil. thick and preferably on the order of at least 2 to 3 mils. thick. This is particularly true where conventional extruding nozzles are employed and the thickness may vary in a reasonable tolerance range resulting in a thinning on one side and a thickening of the other side of the tube, for example.

Various medical-surgical tubings are interconnected to other devices and in some cases requiring a compression clamp connection and other employing a barb type fitting. In applications for compression clamp fittings, a relatively rigid or hard tubing is desired. In contrast for barb type fittings, the softer polyurethane would be desirable. Further, if any one of these layers can, of course, be provided with suitable radial opaque material, if desired.

Further, in accordance with the present invention, additional layers might be employed. For example, a three layer medical-surgical tubing might be provided to provide an inner core with suitable outer protective layers to produce the desired smoothness or flexibility and flow characteristics.

Thus, the present invention provides a highly improved and unique medical-surgical tubing constructed with commercial production processes and equipment and providing inexpensive medical-surgical tubing particularly desirable where high purity and non-migrating characteristics are required.

DESCRIPTION OF DRAWING

The drawing furnished herewith illustrates a preferred construction of the present invention in which the above advantages and features are clearly disclosed as well as others which will be readily understood from the following description.

In the drawing.

DESCRIPTION OF THE ILLUSTRATED EMBODIMENT

Figure 1:
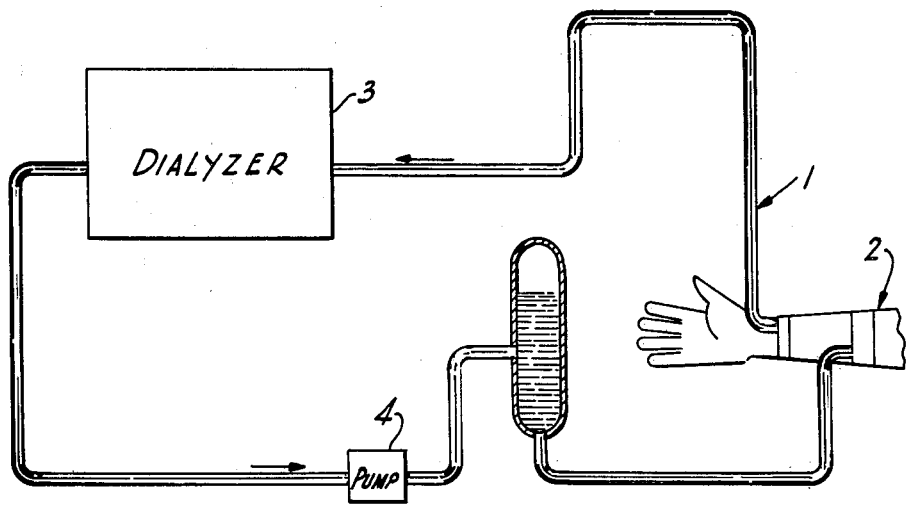
FIG. 1 is an elevational view of a medical-surgical tubing in accordance with the present invention shown connected for providing of blood circulation to and from a patient.
Figure 2:
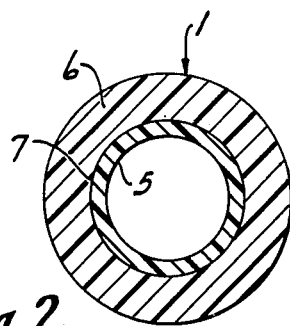
FIG. 2 is an enlarged vertical section generally on line 2—2 of FIG. 1.

Referring to the drawing, the medical-surgical tubing 1 constructed in accordance with the teaching of the present invention is shown interconnecting the artery and veins of a patient's arm 2 to a dialyzer 3. A pump 4 circulates the blood from the arm 2 through the dialyzer 3 and back to the arm. In this application, it is highly important to maintain the inner surface of the tube 1 of a material which will not cause any contamination of the circulating blood. Referring particularly to FIGS. 1 and 2, the cross section of the extruded tubing 1 is seen to include a thin first core or layer 5 and a relatively heavy, thick outer shell or layer 6. Both core and shell are coextruded as integral plastic members which are intimately bonded along the interface 7 to form a single integral tubing. The inner layer or core 5 is formed of polyurethane to present a continuous stable and non-migrating surface which prevents and eliminates possible contamination of the blood. The outer layer or shell 6 is formed of a suitable inexpensive plastic such as polyvinyl chloride. A highly satisfactory polyurethane is that manufactured and sold by the UpJohn Company with the number UpJohn 2363-80A. Generally, any of the 2363 series is suitable for medical-surgical tubing. Hooker Chemical Co. manufactures and sells a polyurethane under the trademark "Rucothane" which can also be employed. The polyvinyl chloride can be any one of the readily available and widely employed materials and any other suitably compound which can be provided by those skilled in the art.

In a practical application for medical-surgical tubing for IV fluids and blood, a tube may be formed with a wall thickness of 30 mils. The inner layer of polyurethane is preferably on the order of 3 mils. to insure a complete inner polyurethane surface. Generally, 1 mil. would be considered a minimum thickness in order to insure the complete coating during coextrusion. The thickness of the polyurethane can, of course, be substantially increased, and subject to the lower limit of 1 mil. may constitute 99% of the total wall thickness.

In a practical application, the tubing will be formed in various sizes in accordance with conventional practice and in most instances the polyurethane will be a significantly thinner layer than that of the alternate low cost plastic. The relative thickness can, of course, be widely varied in accordance with the particular desired characteristic, allowable cost and the like.

As previously noted, polyurethane is a relatively flexible material while vinyl is available as a relatively soft material. By employing a substantial heavy vinyl shell 6 of a suitable low durometer and a thin core 5, a flexible tubing can be provided.

A composite tubing can be readily constructed to have a 60 durometer rating providing a highly desirable thin wall, but highly flexible tubing.

Figure 3:
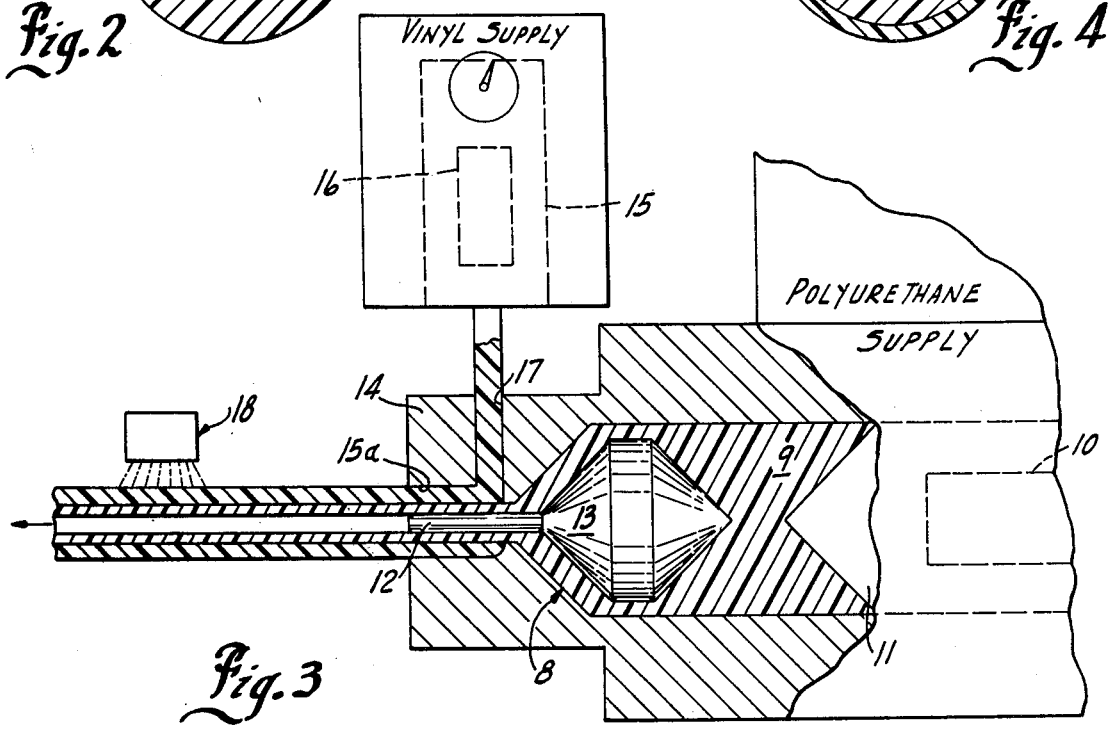
FIG. 3 is a simplified illustration of the extrusion apparatus for forming of the tubing shown in FIGS. 1 and 2.

The tubing may be conveniently formed by employing conventional extruding nozzles mounted in coaxial relation, as diagramatically illustrated in FIG. 3.

Referring particularly to FIG. 3, an inner extrusion nozzle unit 8 of a conventional construction is connected to a polyurethane extruding source 9 and a heating means 10 formed within the coextruder 11 for raising the temperature of a polyurethane. Generally, the nozzle unit includes an inner diameter sizing member 12 and the mandrel 13 is also heated to maintain the necessary curing temperature for the polyurethane. In a practical application, the polyurethane is heated to a temperature of 400° to 450° F.

Concentric with the nozzle 8 is a second nozzle unit 14 which is connected to a polyvinyl chloride extrude 15. The extrude 15 includes a heating unit 16 to raise the polyvinyl chloride temperature to a suitable level for curing. Generally, the polyvinyl chloride will be heated to the order of 300° F. If it were heated to the level of the polyurethane, namely 400° to 450° F. it would rapidly degrade and/or destroy the tubing and prevent creation of an integral medical-surgical tubing.

The nozzle unit 8 is a conical nozzle terminating in the outer forming end and the nozzle 14 is formed concentric with the nozzle unit 8. The polyvinyl chloride is introduced concentrically about the polyurethane nozzle unit 8 such that it is deposited as a layer onto the polyurethane tubing 5. The nozzle unit 14 is provided with an opening 15a determining the final diameter of the medical-surgical tubing. The heated polyvinyl chloride is introduced into nozzle unit 14 through a single opening 17 centrally of the length under a pressurized state by the extruder 15 into the die opening and thus insures a firm, integral laminating of the heated vinyl to the polyurethane tubing 5. The opening 17 connects to an encircling groove on the inner face of the nozzle to introduce the heated plastic into the space between the nozzles and cause such plastic to fill such space. Applicant's teaching thus provides a highly reliable and effective means of depositing polyvinyl chloride or the outer plastic coating or layer onto the inner plastic coating or layer with an intimate bond formed between the layers.

The coextruded tubing 1 is pulled from the nozzle unit in accordance with conventional practice and is also passed through a suitable cooling unit 18 located immediately downstream of the unit 14 to rapidly drop the temperature. Cooling unit 18 may be of any desired or well known construction presently employed in plastic extrusion.

As previously noted, the polyvinyl chloride rapidly degrades at curing temperature of the polyurethane. However, by heating of the polyvinyl chloride to a significantly lower temperature and rapidly removing it from the die area, the degrading effect of the temperature of the hot polyurethane is avoided. The practically instantaneously cooling provided by the special cooling means 18 further insures the reliable formation of the integral tubing 1 in which there is no delamination between the layers 5 and 6.

The relative thickness of the layers may, of course, be relatively determined by the construction of the nozzle, and can be varied widely over various ranges. Further, as previously noted, other multiple layer configurations can be constructed. For example, the polyurethane can be formed on the outer surface of the tubing. For example, the medical-surgical tubing is to be employed as an endo-tubing, the polyurethane would be desirably applied to the outer surface.

Figure 4:
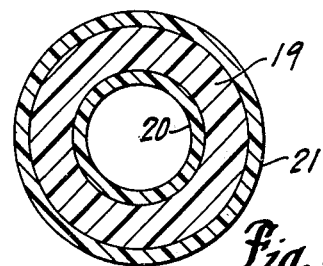
FIG. 4 is a view similar to FIG. 2 showing an alternature multiple layer medical-surgical tubing.

Referring particularly to FIG. 4, a three layer tubing is shown in which a thick body of polyvinyl chloride or the like is sandwiched between inner and outer polyurethane layers.

Further, although the coextrusion of the two different thermoplastic materials provides a highly unique method of forming the novel tubing, particularly in the smaller size tubing for such as 30 mils. diameter, the larger medical-surgical tubing may also be formed by preforming the higher temperature polyurethane tube and then coating such tubing in a cross-head die with the vinyl at the required temperature of the order of 300° F.

The present invention thus provides a low cost, non-migrating medical-surgical tubing which can be conveniently constructed with known, commercially available components and materials.

Various modes of carrying out the invention are contemplated as being within the scope of the following claims, particularly pointing out and distinctly claiming the subject matter which is regarded as the invention.

I claim:

1. The method of forming a non-migratory medical-surgical tubing including a first tube of a first thermoplastic intimately secured onto a second tube of a second thermoplastic, said first and second thermoplastics having distinctly different curing temperatures and the lower temperature cured thermoplastic being adversely effected by the temperature of the higher temperature cured thermoplastic, comprising separately heating said first and second thermoplastics to the corresponding curing temperatures, simultaneously extruding the heated first and second thermoplastics at essentially said temperatures in an extruding apparatus, and cooling the extruded laminated tubing as it emerges from the extruding apparatus for said extruding.

2. The method of forming a non-migratory medical-surgical tubing in accordance with claim 1, selecting said first thermoplastic as polyurethane and said second thermoplastic as polyvinyl chloride said heating includes heating of said polyurethane to a temperature of substantially 425° F. and said polyvinyl chloride to a temperature of substantially 300° F.

3. The method of forming a non-migrating medical-surgical tubing in accordance with claim 1, including selecting of polyurethane as one of said thermoplastics, heating said polyurethane to the curing temperature on the order of 425° F. for said extruding, and said second material having a curing temperature substantially lower than 425° F.

4. The method of forming a non-migratory medical-surgical tubing including extruding a first tube of a polyurethane at its curing temperature, and simultaneously forming a second tube of a second thermoplastic having distinctly different and lower curing temperatures on said extruded polyurethane tube to form a composite tube with an integral interface between the polyurethane and the second plastic, said polyurethane and said second thermoplastic being extruded and formed at the curing temperatures, and cooling of said composite tube essentially immediately after forming of the second tube form said composite tube.

5. The method of forming a non-migratory medical-surgical tubing in accordance with claim 1, including forming said polyurethane with a wall thickness of at least twenty mils, and forming said second tube by forcing of the second plastic at its curing temperature onto said first tube.

* * * * *

UNITED STATES PATENT AND TRADEMARK OFFICE
CERTIFICATE OF CORRECTION

PATENT NO. : 4,211,741
DATED : July 8, 1980
INVENTOR(S) : ELI OSTOICH

It is certified that error appears in the above-identified patent and that said Letters Patent are hereby corrected as shown below:

| | | |
|---|---|---|
| Column 2, | Line 5 | After "of" cancel "relavtively" and substitute therefore --- relatively ---; |
| Column 3, | Lines 30-31 | After "an" cancel "alternature" and substitute therefore --- alternative ---; |
| Column 6, CLAIM 4 | Line 38 | After "tube" insert --- to ---; |
| Column 6, CLAIM 5 | Line 40 | After "claim" cancel "1" and substitute therefore --- 4 ---. |

Signed and Sealed this

Twenty-eighth Day of October 1980

[SEAL]

Attest:

SIDNEY A. DIAMOND

Attesting Officer

Commissioner of Patents and Trademarks